US006783275B2

(12) United States Patent
Ghelmansarai

(10) Patent No.: US 6,783,275 B2
(45) Date of Patent: Aug. 31, 2004

(54) VERIFICATION OF RADIATION AND LIGHT FIELD CONGRUENCE

(75) Inventor: Farhad Abbasi Ghelmansarai, Danville, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 284 days.

(21) Appl. No.: 10/113,676

(22) Filed: Mar. 29, 2002

(65) Prior Publication Data

US 2003/0185348 A1 Oct. 2, 2003

(51) Int. Cl.[7] .................................................. A61B 6/08
(52) U.S. Cl. .......................... 378/206; 378/205; 378/65
(58) Field of Search ................................ 378/206, 205, 378/207, 62, 65, 98.8; 250/370.09

(56) References Cited

U.S. PATENT DOCUMENTS

| | | | | |
|---|---|---|---|---|
| 5,684,854 A | | 11/1997 | Hughes | 378/206 |
| 6,076,966 A | * | 6/2000 | Stueve | 378/207 |
| 6,305,842 B1 | * | 10/2001 | Kunert | 378/206 |
| 6,626,569 B2 | * | 9/2003 | Reinstein et al. | 378/206 |
| 2002/0181660 A1 | * | 12/2002 | Reinstein et al. | 378/205 |

OTHER PUBLICATIONS

The Quality Control Phantom QC–3: QC–3V Test Phantom, download from http://www.go–pips.com/html/phantom.html on Mar. 4, 2002, 3pgs.
Quality Assurance Tools: IBC III Isocentric Beam Checker III, Catalog #9320, download from http://www.micknuclear.com/page17.html on Mar. 4, 2002, 3pgs.
Visi–X—for checking light and radiation field coincidence on X–Ray equipment, download from http://www.barker-net.com/products/x–ray/visi–x/index.htm on Mar. 5, 2002, 1pg.
Quality Assurance Tools: IBC I Isocentric Beam Checker I, Catalog #7801, download from http://www.micknuclear.com/page15.html on Mar. 4, 2002, 4pgs.
Laboratory Exercise 2, download from http://www.radiotherapy.wisc.edu/education/mp566/labs/exercise2.html on Mar. 4, 2002. 5pgs.
Keith T. Welsh et al., Automated Image Based Quality Assurance for Medical Linear Accelerators, 3pgs.
Michael C. Kirby, "A multipurpose phantom for use with electronic portal imaging devices", Phys. Med. Biol. 40 © 1995, pp. 323–334.
K. Luchka et al., "Assessing radiation and light field congruence with a video based electronic portal imaging device", Medical Physics, vol. 23, No. 7, Jul. 1996, © 1996 Am. Assoc. Phys. Med., pp. 1245–1252.

* cited by examiner

*Primary Examiner*—Craig E. Church
*Assistant Examiner*—Irakli Kiknadze

(57) ABSTRACT

A system for determining congruence of a light field and a radiation field includes acquisition of first electronic image data representing a phantom as illuminated by light emitted by a light emitter, acquisition of second electronic image data representing the phantom as irradiated by treatment radiation emitted by the treatment radiation emitter, and determination of congruence of a light field produced by the light emitter and a treatment radiation field produced by the treatment radiation emitter based on the first electronic image data and the second electronic image data.

25 Claims, 11 Drawing Sheets

VERIFICATION OF RADIATION AND LIGHT FIELD CONGRUENCE

BACKGROUND

1. Field

The present invention relates generally to radiation treatment, and more particularly to calibrating systems to be used during such treatment.

2. Description

Conventional radiation treatment typically involves directing a radiation beam at a tumor in a patient to deliver a predetermined dose of treatment radiation to the tumor according to an established treatment plan. A suitable radiation treatment device is described in U.S. Pat. No. 5,668,847, issued Sep. 16, 1997 to Hernandez, the contents of which are incorporated herein for all purposes.

Healthy tissue and organs are often in the treatment path of the radiation beam during radiation treatment. The healthy tissue and organs must be taken into account when delivering a dose of radiation to the tumor, thereby complicating determination of the treatment plan. Specifically, the plan must strike a balance between the need to minimize damage to healthy tissue and organs and the need to ensure that the tumor receives an adequately high dose of radiation. In this regard, cure rates for many tumors are a sensitive function of the radiation dose they receive.

Treatment plans are therefore designed to maximize radiation delivered to a target while minimizing radiation delivered to healthy tissue. If the radiation is not delivered exactly as required by the treatment plan, the goals of maximizing target radiation and minimizing healthy tissue radiation may not be achieved. More specifically, errors in radiation delivery can result in low irradiation of tumors and high irradiation of sensitive healthy tissue. The potential for mis-irradiation increases with increased delivery errors.

To ensure that radiation will be delivered to a proper area, a light field is used to indicate the position of a field within which radiation will be delivered. In particular, light is projected onto a patient to create a light field and an operator determines whether the light field delineates an area to which radiation is to be delivered according to a treatment plan. Accordingly, the light field is assumed to be located at a same position as a radiation field within which radiation will be delivered during radiation treatment.

Delivery errors may occur if the light field is not located at a same position as the subsequently-produced radiation field. Accordingly, it is necessary to verify that the position of the light field accurately represents a position of the radiation field. Conventionally, this verification is performed by illuminating X-ray film with the light field, marking the film at the edges of the light field, exposing the film to radiation, and comparing the location of the radiation field as appearing on the exposed film with the location of the marks. This system is unacceptably susceptible to the radiation field penumbra, the brightness and blurriness of the light field, and to human error in marking the film and measuring the difference in the fields.

Other systems to verify congruence between the light field and the radiation field have been proposed by Luchka et al, "Assessing radiation and light field congruence with a video-based electronic portal imaging device", Med. Phys 23 (7), July 1996, pgs 1235–1252, by Kirby, "A multipurpose phantom for use with electronic portal imaging devices", Phys. Med. Biol. 40, 1995, pgs. 323–334, and by others, but none of these systems provides desirable accuracy and efficiency.

It would therefore be beneficial to provide a system and method to efficiently and effectively verify congruence between a light field and a radiation field used for radiation treatment. When used in conjunction with conventionally-designed treatments, more accurate congruence reduces the chance of harming healthy tissue. More accurate congruence also allows the use of more aggressive treatments. Specifically, if a margin of error in field congruence is known to be small, treatment may be designed to safely radiate a greater portion of a tumor with higher doses than in scenarios where the margin of error is larger.

SUMMARY

To address at least the above problems, some embodiments of the present invention provide a system, method, apparatus, and means to determine congruence of a light field and a radiation field through acquisition of first electronic image data representing a light field produced by a light emitter, acquisition of second electronic image data representing a radiation field produced by a treatment radiation emitter, and determination of a congruence between the light field and the radiation field based on the first data and the second data.

In some embodiments, the present invention provides acquisition of first electronic image data representing a phantom located at a first position and illuminated by light emitted by a light emitter, acquisition of second electronic image data representing the phantom located at the first position and irradiated by treatment radiation emitted by a treatment radiation emitter, normalization of the first electronic image data and the second electronic image data to account for differences in divergence properties of the emitted light and the emitted treatment radiation, generation of superimposed electronic image data based on the first normalized electronic image data and the second normalized electronic image data, determination of a distance between a location of a hole of the phantom as represented by the first normalized electronic image data and a location of the edge of the phantom as represented by the second normalized electronic image data based on the superimposed electronic image data, and determination of congruence of a light field produced by the light emitter and a treatment radiation field produced by the treatment radiation emitter based on a difference between the distance and an actual corresponding distance between the hole and the edge of the phantom.

According to some embodiments, the present invention provides acquisition of first waveforms representing a phantom located at a first position as illuminated by light emitted by a light emitter, acquisition of second waveforms representing the phantom located at the first position as irradiated by treatment radiation emitted by a treatment radiation emitter, normalization of the first waveforms and the second waveforms to account for differences in divergence properties of the emitted light and the emitted treatment radiation, determination of a first location of a hole of the phantom based on the first normalized waveforms, determination of a second location of the hole of the phantom based on the second normalized waveforms, and determination of the congruence between the light field and the radiation field based on a difference, if any, between the first location and the second location.

In some aspects, the present invention provides acquisition of first electronic image data representing a light field produced by a light emitter, acquisition of second electronic image data representing a radiation field produced by a treatment radiation emitter, acquisition of first reference electronic image data representing a reference light field produced by the light emitter, acquisition of second reference electronic image data representing a reference radiation field produced by the treatment radiation emitter, determination of a first location of a hole of the phantom based on the first reference electronic image data, determination of a second location of the hole of the phantom based on the second reference electronic image data, determination of a third location of the hole of the phantom based on the first electronic image data, determination of a fourth location of the hole of the phantom based on the second electronic image data, and comparison of a distance between the first location and the second location with a distance between the third location and the fourth location.

In still other aspects, provided are acquisition of first reference electronic image data representing a reference light field produced by a light emitter, the first reference electronic image data comprising third waveforms representing a phantom as illuminated by the reference light field, acquisition of second reference electronic image data representing a reference radiation field produced by a treatment radiation emitter, the second reference electronic image data comprising fourth waveforms representing the phantom as irradiated by the reference radiation field, acquisition of first electronic image data representing a light field produced by the light emitter and comprising first waveforms representing the phantom as illuminated by the light field, acquisition of second electronic image data representing a radiation field produced by the treatment radiation emitter and comprising second waveforms representing the phantom as irradiated by the radiation field, comparison of a location of a hole of the phantom according to the first waveforms with a location of the hole according to the third waveforms, and comparison of a location of the hole of the phantom according to the second waveforms with a location of the hole according to the fourth waveforms.

The present invention is not limited to the disclosed embodiments, however, as those of ordinary skill in the art can readily adapt the teachings of the present invention to create other embodiments and applications.

BRIEF DESCRIPTION OF THE DRAWINGS

The exact nature of this invention, as well as its objects and advantages, will become readily apparent from consideration of the following specification as illustrated in the accompanying drawings, in which like reference numerals designate like parts, and wherein.

DETAILED DESCRIPTION

The following description is provided to enable any person of ordinary skill in the art to make and use the invention and sets forth the best modes contemplated by the inventor for carrying out the invention. Various modifications, however, will remain readily apparent to those in the art.

Figure 1:
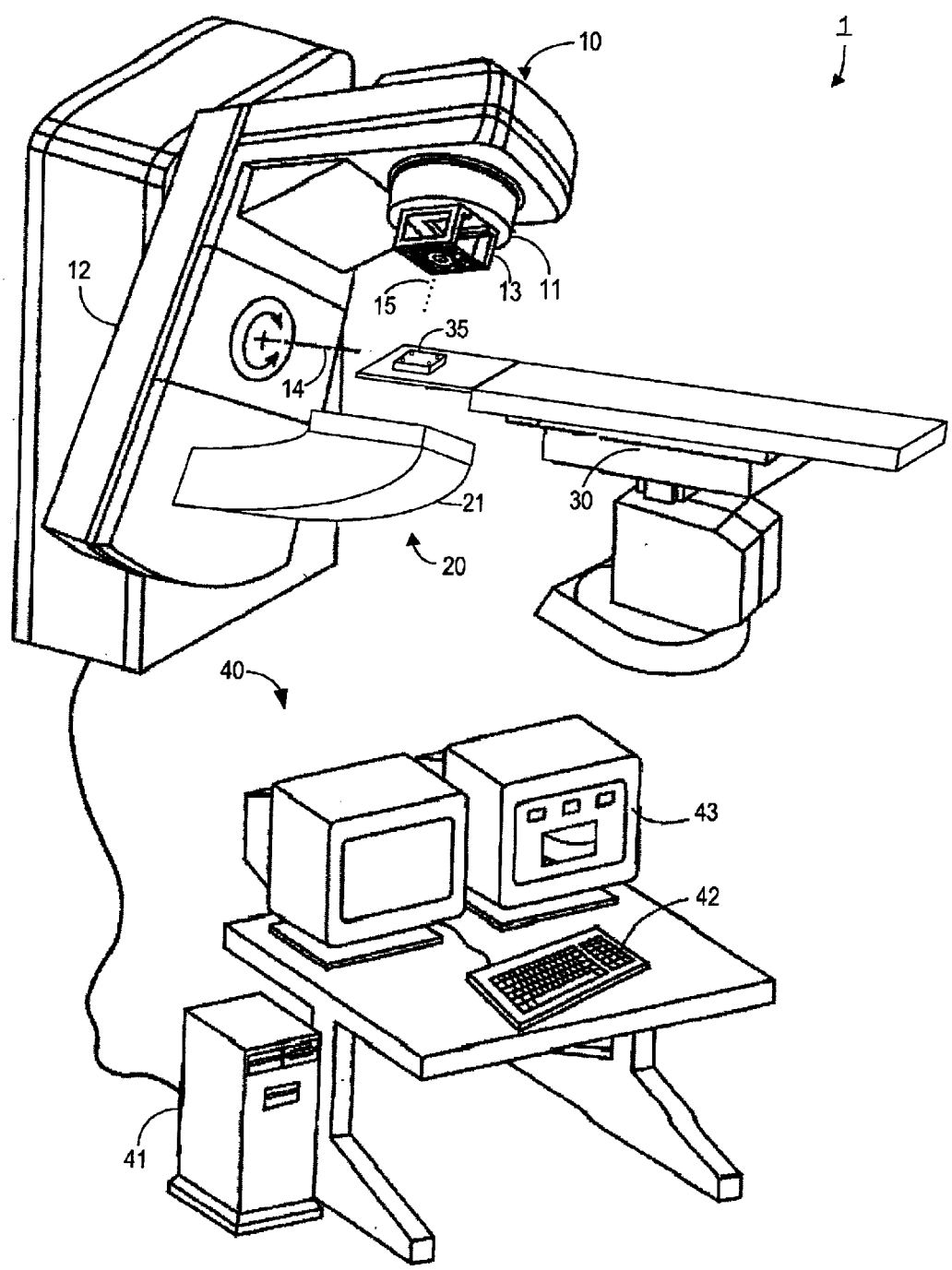
FIG. 1 is diagram illustrating a radiation treatment room according to some embodiments of the present invention.

FIG. 1 illustrates radiation treatment room 1 pursuant to some embodiments of the present invention. Radiation treatment room 1 includes linear accelerator (linac) 10, imaging device 20, treatment table 30 and operator station 40. The elements of radiation treatment room 1 are used to deliver treatment radiation to a patient according to a radiation treatment plan.

Linac 10 delivers treatment radiation to a treatment area and is primarily composed of treatment head 11 and gantry 12. Accessory tray 13 is mounted on treatment head 11 and may be configured to receive and securely hold attachments used during the course of treatment planning and treatment (such as, for example, reticles, wedges, or the like). Treatment head 11 also includes a beam-emitting device for emitting treatment radiation and a beam-shielding device, or collimator, for shaping the radiation and for shielding sensitive surfaces therefrom. The treatment radiation may comprise electron, photon or any other type of radiation.

Treatment head also includes a light-emitting device such as a light bulb. The light bulb is used as described above to produce a light field that is used to confirm a location of a radiation field to be delivered. In this regard, the term "light" will be used to describe the radiation emitted from the light bulb and used to produce a light field. On the other hand, the terms "treatment radiation" and "radiation" will be used herein to identify radiation emitted by the beam-emitting device and used to treat a patient.

Treatment head 11 is fastened to a projection of gantry 12. Gantry 12 is rotatable around axis 14 before, during and after radiation treatment. During such treatment, radiation is delivered from linac 10 to the beam-emitting device of treatment head 11 and emitted therefrom along beam path 15. The delivered radiation is focused on a point, known as the isocenter, which is located at the intersection of beam path 15 and axis 14. Due to divergence of the emitted radiation and shaping of the radiation by the collimator leaves, the radiation is delivered to a radiation field rather than only to the point upon which the radiation is focused.

Imaging device 20 acquires images that are used before, during and after radiation treatment. More particularly, imaging device 20 is used to acquire images for verification and recordation of a patient position and an internal patient portal to which radiation is delivered. These images are used to ascertain that the patient position, as well as the shape and size of the radiation field, conform to a desired treatment plan.

Images acquired by imaging device 20 may also be used according to some embodiments of the invention to verify congruence of a light field and a radiation field produced by linac 10. As described above, a light field is used during patient positioning to simulate a location of a radiation field to be delivered. Accordingly, it is important that the location of the light field corresponds as closely as possible to the location of the radiation field produced by linac 10. Examples of techniques for verifying field congruence according to some embodiments of the invention are set forth in detail below.

In some embodiments, imaging device 20 comprises light-proof housing 21 within which are disposed a scintillator, a mirror and a CCD (or tube) camera. Generally, imaging device 20 may be used to acquire images of items irradiated by light and/or treatment radiation. Housing 21 may be attached to gantry 12 in any manner, and may include an extendible and retractable structure. Pursuant to some embodiments of the present invention, this structure may be used to advance and retract imaging device 20 to and from an imaging position along beam path 15 in order to acquire images required for treatment. According to some embodiments, imaging device 20 comprises the BEAM-VIEW™ system produced by the present assignee. Further details of the structure and operation of imaging device 20 according to some embodiments of the invention are set forth below with respect to FIG. 2.

Table 30 supports a patient during radiation treatment. Table 30 is adjustable to ensure, along with rotation of gantry 12, that an area of the patient that is to be treated is positioned at the isocenter. In this regard, located at the isocenter of linac 10 in FIG. 1 is phantom 35. Phantom 35 is used as described below to verify congruence between a light field and a radiation field produced by linac 10. Properties of phantom 35 will be discussed with respect to FIG. 3.

Operator station 40 includes a processor 41 in communication with an input device such as keyboard 42 and an operator console 43 (including one or more visual display units or monitor). Operator station 40 is typically operated by an operator who administers actual delivery of radiation treatment as prescribed by an oncologist. The operator uses keyboard 42 to perform calibration procedures including verification of field congruence and acquisition of data used for image correction, to input data defining a radiation dose to be delivered to the patient, and to deliver treatment radiation to the patient. The data may also be input via another input device, such as a data storage device. Operator console 42 displays data to the operator before, during and after the treatment.

Operator station 40 may be located apart from linac 10, such as in a different room, in order to protect the operator from radiation. For example, linac 10 may be located in a heavily shielded room, such as a concrete vault, which shields the operator from radiation generated by linac 10.

Processor 41 may store processor-executable process steps according to some embodiments of the present invention. In some aspects, the process steps are executed by processor 41, linac 10, imaging device 20, and/or another device to determine congruence of a light field and a radiation field through acquisition of first electronic image data representing a light field produced by a light emitter, acquisition of second electronic image data representing a radiation field produced by a treatment radiation emitter, and determination of a congruence between the light field and the radiation field based on the first data and the second data.

The process steps may also be executed provide acquisition of first electronic image data representing a phantom located at a first position and illuminated by light emitted by a light emitter, acquisition of second electronic image data representing the phantom located at the first position and irradiated by treatment radiation emitted by a treatment radiation emitter, generation of superimposed electronic image data based on the first electronic image data and the second electronic image data, determination of a distance between a location of a hole of the phantom and a location of the edge of the phantom based on the superimposed electronic image data, and determination of a congruence of a light field produced by the light emitter and a treatment radiation field produced by the treatment radiation emitter based on a difference between the distance and an actual corresponding distance between the hole and the edge of the phantom.

According to some embodiments, the process steps provide acquisition of first waveforms representing a phantom located at a first position as illuminated by light emitted by a light emitter, acquisition of second waveforms representing the phantom located at the first position as irradiated by treatment radiation emitted by a treatment radiation emitter, normalization of the first waveforms and the second waveforms, determination of a first location of a hole of the phantom based on the normalized first waveforms, determination of a second location of the hole of the phantom based on the normalized second waveforms, and determination of the congruence between the light field and the radiation field based on a difference, if any, between the first location and the second location.

The above-described steps may also be embodied, in whole or in part, by hardware of processor 41, linac 10, imaging device 20. Moreover, embodiments of the invention may be embodied by hardware and/or software of a standalone device connected between imaging device 20 and operator station 40, between linac 10 and imaging device 20, or elsewhere.

Of course, each of the devices shown in FIG. 1 may include less or more elements than those shown. Moreover, transformation and storage of acquired data may be performed by any one or more of the devices. In addition, embodiments of the invention are not limited to the devices shown.

Figure 2:
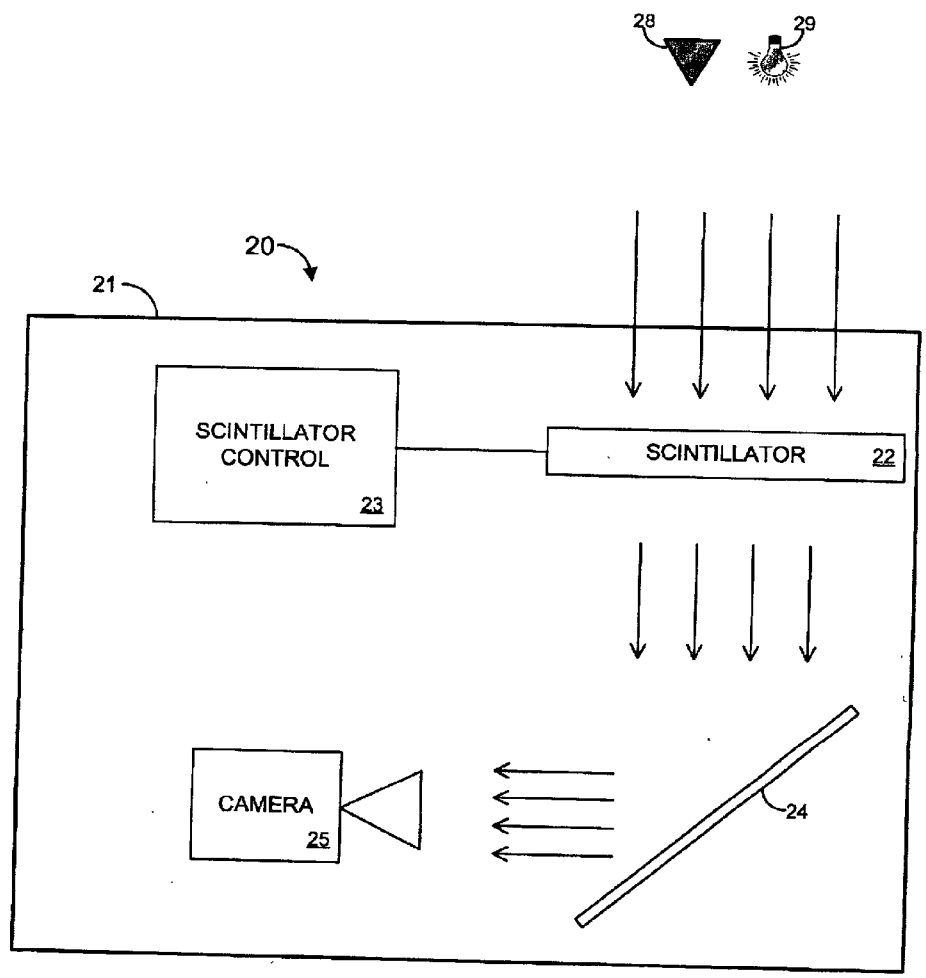
FIG. 2 is a diagram illustrating elements of an imaging device according to some embodiments of the present invention.

FIG. 2 is a diagram illustrating elements of imaging device 20 according to some embodiments of the invention. As shown, imaging device 20 consists of housing 21, scintillator 22, scintillator control 23, mirror 24, and camera 25. Housing 21 is designed so that no light can enter imaging device 20 when scintillator 22 is in the position shown. In this regard, also shown in FIG. 2 are treatment radiation emitter 28 and light bulb 29, both of which are disposed within treatment head 11.

Scintillator 22 may be composed of gadolinium-oxisulfide or Cesium-iodide scintillator material. By virtue of its composition, scintillator 22 absorbs treatment radiation emitted by treatment radiation emitter 28 and emits visible photons having an intensity proportional to that of the absorbed radiation toward mirror 24. Accordingly, the photons are reflected toward camera 25, thereby allowing camera 25 to acquire an image representing a radiation field produced by radiation emitter 28. Such an image would also represent any object that is not completely transparent to the treatment radiation and that is placed between radiation emitter 28 and scintillator 22.

Scintillator control 23 consists of hardware and/or software to move scintillator 22 so that light emitted by light bulb 29 can pass directly to mirror 24. This light is then reflected toward camera 25, enabling camera 25 to acquire an image representing a light field produced by light bulb 29. As a result, imaging device 20 is capable of acquiring an image also representing an object disposed between light bulb 29 and mirror 24 and illuminated by light emitted from light bulb 29. In some embodiments, scintillator 22 is manually removed from imaging device 20 so that light emitted by light bulb 29 can pass directly to mirror 24.

In a case that camera 25 produces a video signal, imaging device 20 may include a frame grabber to read the video signal in real-time and produce still frames therefrom. Still frame images may be output from imaging device 20 to acquisition and image processing software executed by processor 41 or by another device and may alternatively or additionally be output to an operator through console 43.

Figure 3:
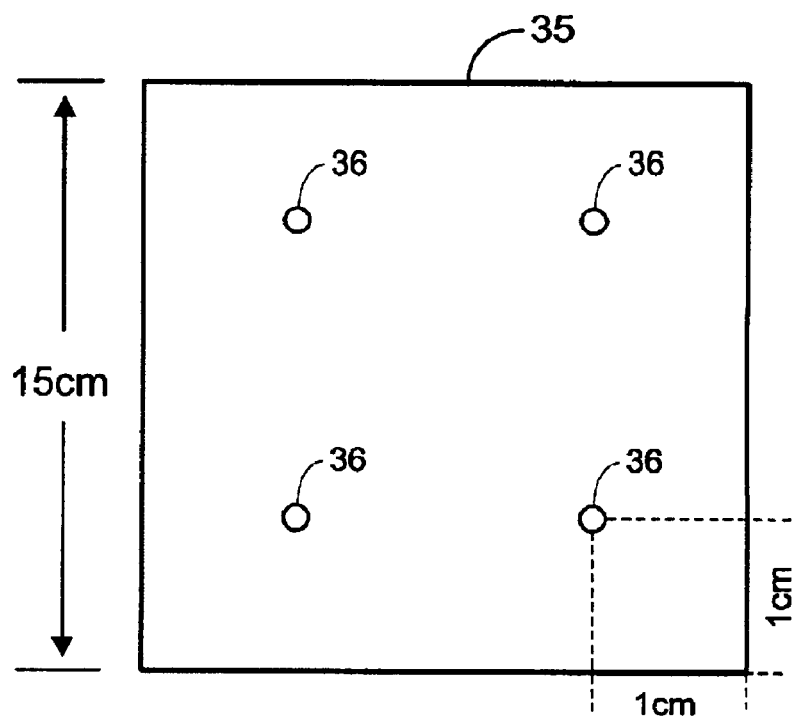
FIG. 3 is a view of a phantom used to verify field congruence according to some embodiments of the present invention.

FIG. 3 is a representative top view of phantom 35 according to some embodiments of the invention. Phantom 35 of FIG. 3 is a 15 cm×15 cm square plate composed of a metal such as steel or aluminum. It should be noted that phantom 35 may be composed of any material having light and treatment radiation stopping power suitable to create images for use in conjunction with embodiments of the present invention. In this regard, the thickness of phantom 35 may be determined based on the stopping power of the material from which it is constructed. Phantom 35 includes four holes 36, each of which is located 1 cm from the two nearest edges of phantom 35. Other phantoms having different shapes and openings may be used in conjunction with the present invention.

Figure 4:
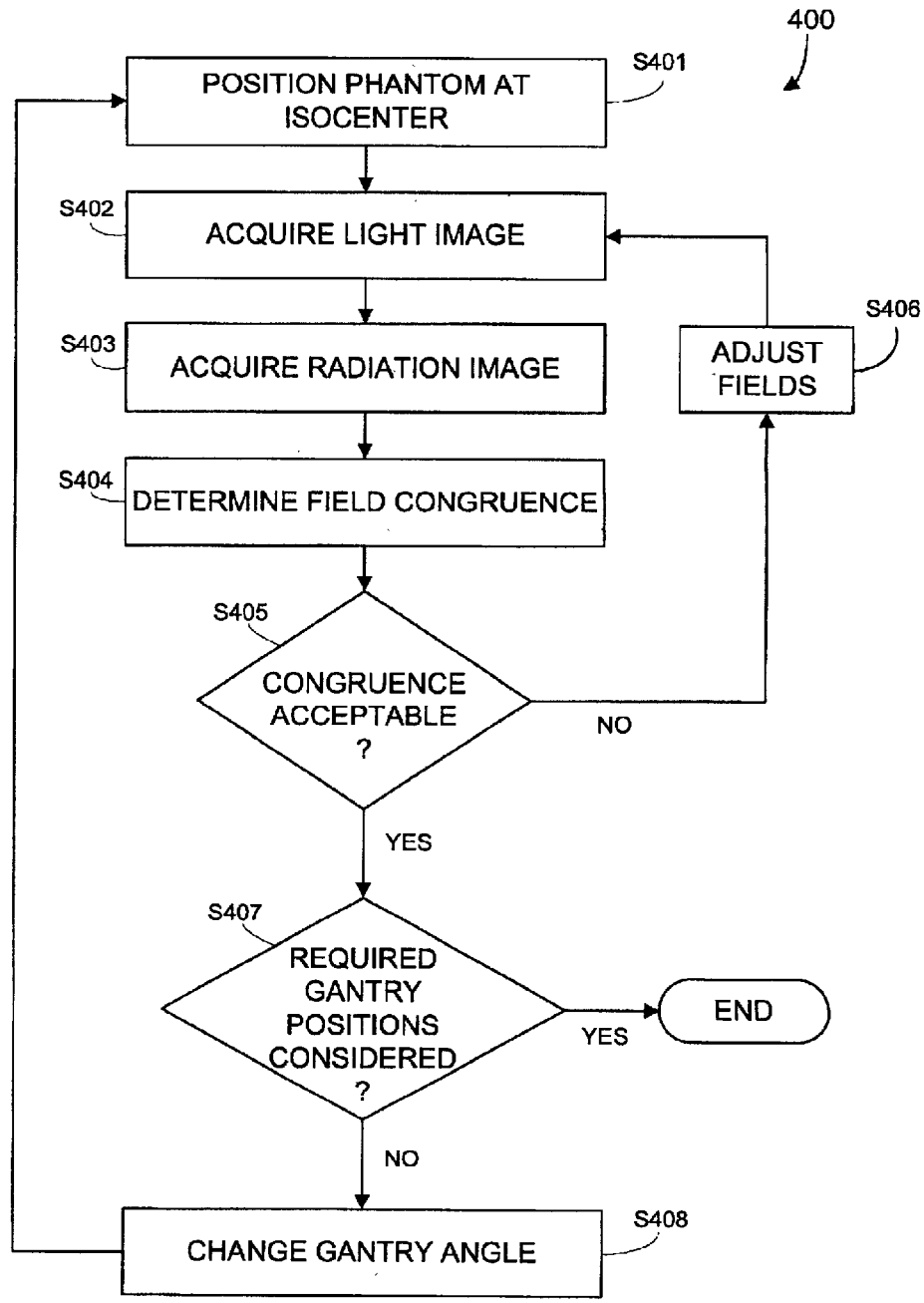
FIG. 4 is a flow diagram illustrating process steps according to some embodiments of the present invention.

FIG. 4 is a flow diagram of process steps 400 according to some embodiments of the invention. Process steps 400 may be embodied by hardware and/or software of processor 41, linac 10, imaging device 20, and/or another device in direct or indirect communication with imaging device 20. Briefly, some embodiments of process steps 400 comprise steps to determine congruence of a light field and a radiation field through acquisition of first electronic image data representing a light field produced by a light emitter, acquisition of second electronic image data representing a radiation field produced by a treatment radiation emitter, and determination of a congruence between the light field and the radiation field based on the first data and the second data.

Initially, in step S401, phantom 35 is positioned on table 30 at the isocenter of linac 10. According to some embodiments, phantom 35 is positioned so that its upper surface is normal to beam 15. Such positioning is contrary to that shown in FIG. 1, where beam 15 does not intercept the upper surface of phantom 35 at a ninety-degree angle.

In some embodiments, light bulb 29 is controlled to emit light and to thereby project a light field onto table 30. A collimator is controlled so that the light field comprises a 15 cm×15 cm square. Phantom 35 is therefore positioned in step S401 so that its position coincides with the projected light field. Phantom 35 is also positioned between treatment radiation emitter 28 and imaging device 20, and between bulb 29 and imaging device 20. "Between" in this sense simply refers to any position allowing the projection of light and/or radiation onto phantom 35 and allowing device 20 to intercept light or radiation passing through phantom 35.

Next, in step S402, a light image comprising electronic image data is acquired. Specifically, scintillator control 23 moves scintillator 22 out of the light path between bulb 29 and mirror 24. Next, all lights in treatment room 1 are extinguished so that the acquired image will represent only light from bulb 29. Bulb 29 and its associated collimator are then controlled to produce a 15 cm×15 cm light field. The field is reflected by mirror 24 and a corresponding image is acquired by camera 25. The light image represents the projected light field and phantom 35 as illuminated by the light field.

Figure 5:
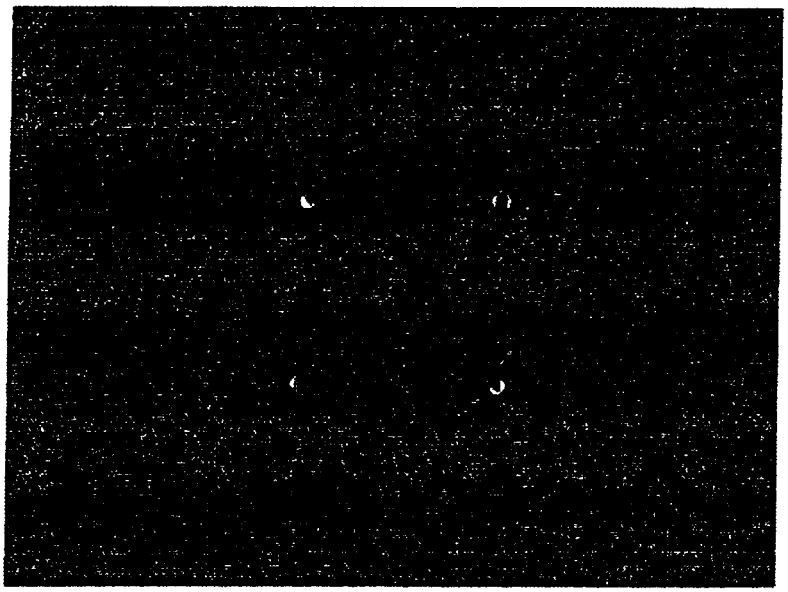
FIG. 5 is a view of a light image according to some embodiments of the present invention.

FIG. 5 depicts an image acquired according to some embodiments of step S402. The FIG. 5 image represents light emitted by light bulb 29 which passed through holes 36 of phantom 35. As shown, no other light passed around the edges of phantom 35 to mirror 24.

A radiation image is then acquired in step S403. To acquire the radiation image, scintillator control 23 moves scintillator 22 into the position shown in FIG. 2 and radiation emitter 28 and an associated collimator are controlled to emit treatment radiation in order to project a 15 cm×15 cm radiation field onto phantom 35. In some embodiments, the emitted radiation corresponds to a dose of 100 cGy. The radiation is received, either attenuated or not, by scintillator 22, which produces light photons having an intensity proportional to the intensity of the received radiation. The produced photons are reflected by mirror 24 and acquired as a radiation image by camera 25.

Figure 6:
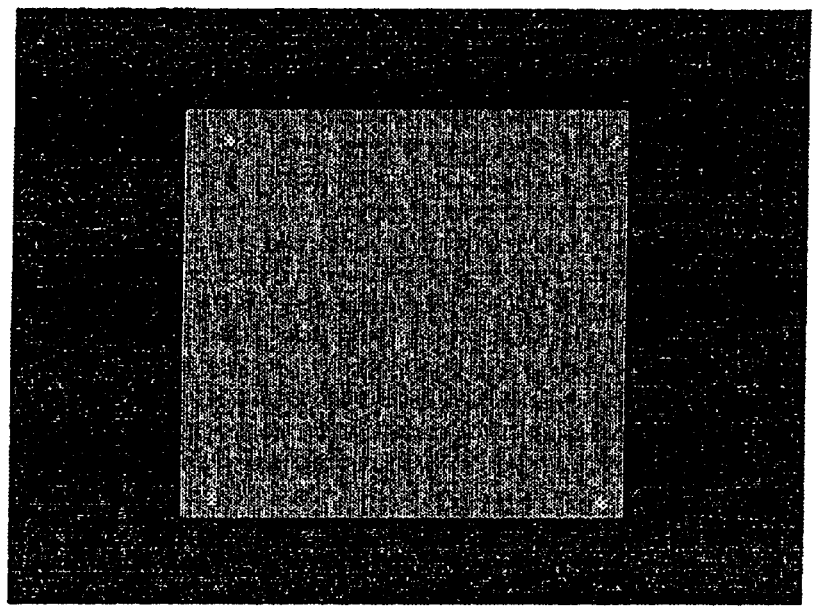
FIG. 6 is a view of a radiation image according to some embodiments of the present invention.

FIG. 6 shows a radiation image according to some embodiments of step S403. The image represents phantom 35 as located at a same position as it was located during acquisition of the light image and as irradiated by the radiation field. The location of the radiation field can be determined from the FIG. 6 image. If, for example, a portion of the radiation field intercepted table 30 at a location not covered by phantom 35, this portion of the field would appear brighter in the radiation image than portions within the area of phantom 35, because the radiation delivered to this portion would not be attenuated to the same degree.

Figure 7:
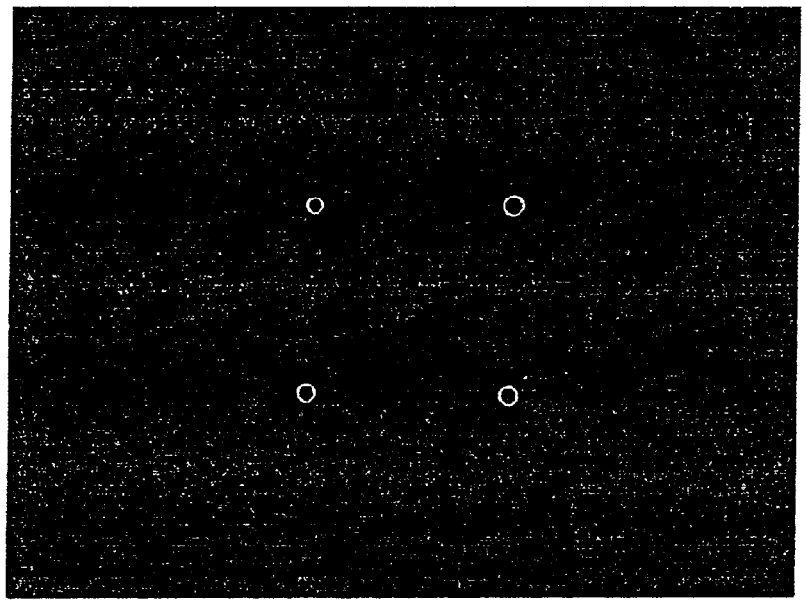
FIG. 7 is a view of a light image after edge detection according to some embodiments of the present invention.

Congruence of the light field and the radiation is determined in step S404. According to some embodiments, this determination initially proceeds by performing edge detection processing on the images acquired in steps S402 and S403. FIG. 7 depicts the acquired light field image after it is subjected to edge detection. As shown, the edges of the lighter areas representing the holes are more clearly delineated in FIG. 7 than in FIG. 5. Similarly, FIG. 8 shows the acquired radiation image after edge detection processing, in which the edges of the radiation field are more clearly evident than as shown in FIG. 6.

Figure 8:
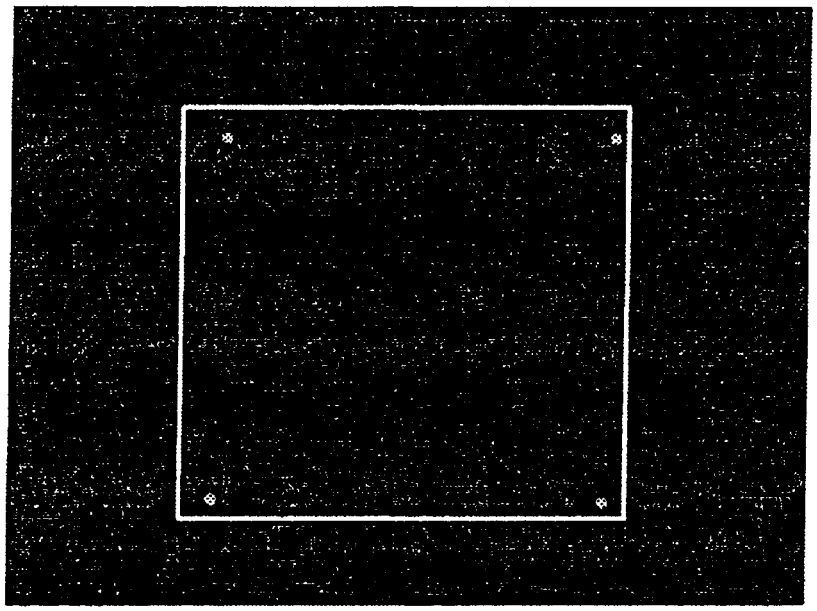
FIG. 8 is a view of a radiation image after edge detection according to some embodiments of the present invention.

As shown, FIG. 8 includes four light-colored areas near the phantom edges. These areas represent are created by treatment radiation passing through holes 36 of phantom 35 during acquisition of the radiation image. Other light-colored spots shown in FIG. 8 are radiation artifacts caused by dead pixels or spots on mirror 24, camera 25 or elsewhere.

Figure 9:
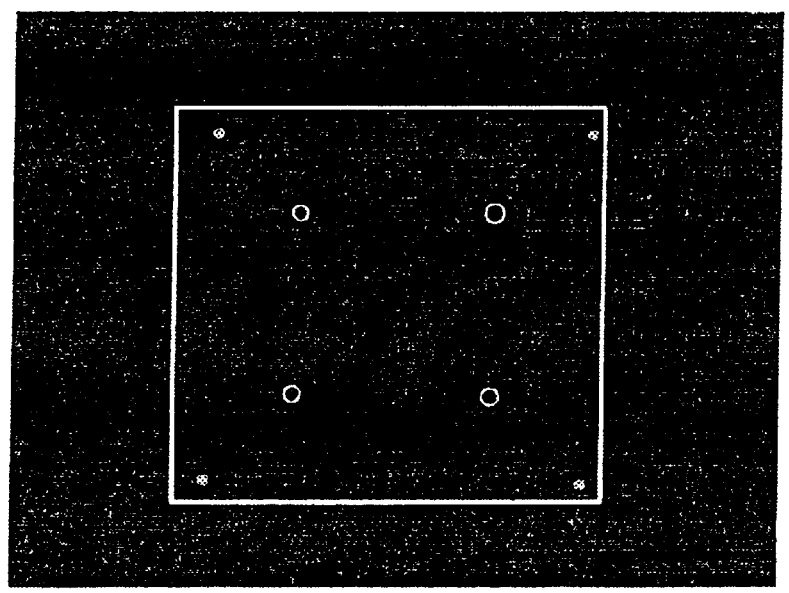
FIG. 9 is a view of a superimposed image according to some embodiments of the present invention.

The edge-detected images are then combined to produce a superimposed image such as that shown in FIG. 9. The combination may comprise subtraction of the images. As shown in FIG. 9, locations of holes 36 as represented by the light image are much different from locations of holes 36 as represented by the radiation image. Accordingly, to determine a congruence between the light field and the radiation field, some embodiments involve normalization of the light image and the radiation image. Such normalization accounts for differences in divergence properties of the emitted light and the emitted treatment radiation. In this regard, differences in the divergence of the light emitted from bulb 29 and the treatment radiation emitted from emitter 28 may cause the acquired radiation image to appear larger than the light field image, even if both fields have equal dimensions in a plane normal to beam 15 and including the isocenter.

For example, each of the acquired light image and the acquired radiation image may be normalized to remove any magnification thereof resulting from the travel of the light and radiation, respectively, from table 30 to imaging device 20. In some embodiments, normalization includes altering one of the radiation image and the light image so that the magnification thereof is equal to that of the other. Because neither phantom 35 nor camera 25 are moved between acquisition of the light image and the radiation image, a single point of phantom 35 will be represented by a same image pixel in both the light image and the radiation image, once differences in beam divergence are taken into account through normalization. After the images are normalized, congruence can be determined by determining a location of a hole as represented by the light image, determining a location of an edge as represented by the radiation image, and comparing a distance between the location of the hole and the location of the edge with an actual corresponding distance of phantom 35. Because dimensions of each pixel at the isocenter are known (e.g., 0.6 mm×0.5 mm for an image of 512×480 pixels) a distance represented within the superimposed image can be accurately determined by counting a number of pixels spanning the distance.

In some embodiments, the light image and the radiation image are not normalized in step S404. Rather, a reference light image and a reference radiation image are acquired prior to step S401 at an instance in which the congruence of the light field and the radiation field is satisfactory. The reference images are combined as described above and, in step S404, the image of FIG. 9 is compared with the combined image. Specifically, distances represented in the FIG. 9 image are compared with corresponding distances of the superimposed reference image to determine if the relative positions of the light and radiation fields differ from that shown by the superimposed reference image. In some examples, one compared distance is the distance from a location of a hole of phantom 35 as represented by the light image to a location of the hole of phantom 35 as represented by the radiation image.

Figure 10A:
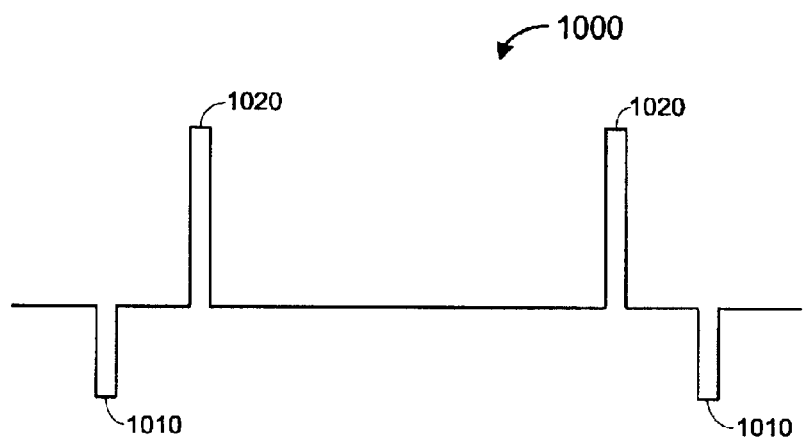
FIG. 10A illustrates a waveform representing a horizontal line of a light image according to some embodiments of the present invention.

In an example according to some embodiments of the invention, image data is acquired in steps S402 and S403 by an oscilloscope that receives a video signal from camera 25. FIG. 10A illustrates waveform 1000, which corresponds to a horizontal scan line acquired during step S402. As shown, waveform 1000 includes horizontal sync pulses 1010 generated by camera 25 and two pulses 1020 corresponding to light passing through holes 36 of phantom 35. Accordingly, waveform 1000 corresponds to a scan line located at a same horizontal position as holes 36.

It should be noted that, in a case that a portion of a light field used to acquire waveform 1000 intercepted table 30 outside of a vertical edge of phantom 35, waveform 1000 would include a pulse having substantially the same amplitude as pulses 1020 and located at a same position relative to pulses 1020 as the vertical edge. Because the horizontal scan time of waveform 1000 is known, a size of the portion of the light field that intercepted table 30 can be determined from the interval of the pulse that represents the portion.

Figure 10B:
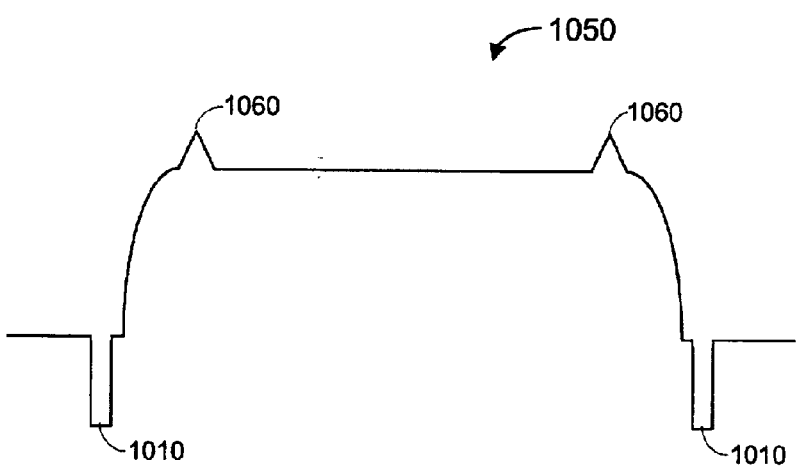
FIG. 10B illustrates a waveform representing a horizontal line of a radiation image according to some embodiments of the present invention.

FIG. 10B illustrates waveform 1050 that is acquired during step S403 according to the some embodiments. Waveform 1050 also represents a horizontal line of phantom 35 that includes two holes 36. Waveform 1050 includes peaks 1060 which represent radiation that passed through holes 36 with less attenuation than radiation that passed through surrounding material of phantom 35.

As described with respect to waveform 1000, any portion of a radiation field overlapping a vertical edge of phantom 35 may be measured using a width of a pulse of waveform 1050 that represents the portion. However, such a pulse will have a greater amplitude than the pulses of waveform 1050 because the overlapped portion will not be attenuated by phantom 35.

In some embodiments, waveforms 1000 and 1050 are normalized as described above. Horizontal positions of holes 36 can then be determined from waveform 1000 by counting a time period between initial pulse 1010 and each of pulses 1020, and by multiplying the periods by a scan speed. The horizontal positions can be similarly calculated from waveform 1050. The positions calculated using waveform 1000 are than compared with the positions calculated using waveform 1050 to determine horizontal congruence of the light field and the radiation field.

Figure 11:
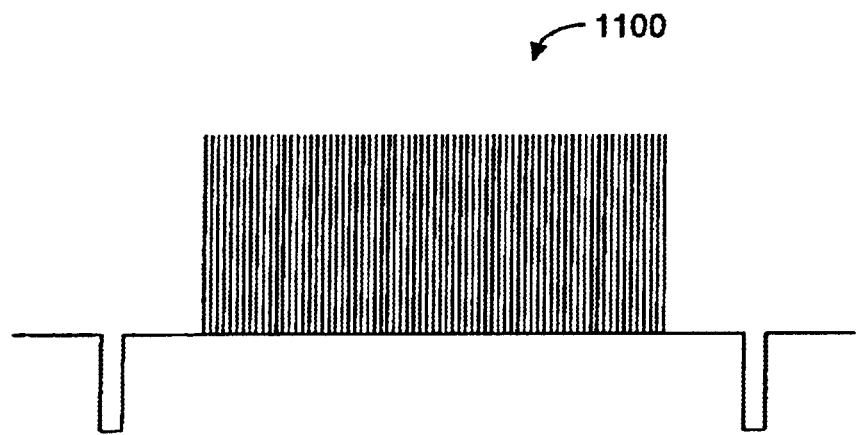
FIG. 11 illustrates a waveform representing a waveform representing each horizontal line of a light image according to some embodiments of the present invention.

To determine vertical congruence using normalized waveforms according to some embodiments of the invention, a field (if camera 25 is interlaced) or a frame (if camera 25 is non-interlaced) waveform such as waveform 1100 of FIG. 11 is acquired in step S402 and step S403. Waveform 1100 consists of all horizontal scan lines of an acquired image, with the uppermost horizontal scan line represented by a left edge of waveform 1100. Using a time delay generator, each horizontal scan line within waveform 1100 can be expanded and viewed. Accordingly, to determine a vertical position of a hole of the light image with respect to a horizontal edge of the light field, one can count a number of lines from the uppermost line of the image to a horizontal line representing the hole. The number of lines is multiplied by a vertical distance represented by each line, which in turn is calculated based on the image size and the field (or frame) scan time. This procedure can also be used to determine a vertical distance between a hole of the radiation image and the edge of the radiation field.

In some other embodiments, reference waveforms are acquired as described above with respect to reference images. Accordingly, congruence is determined by comparing locations of holes 36 according to waveform 1000 with locations of holes 36 according to the reference light waveform, and by comparing locations of holes 36 according to waveform 1050 with locations of holes 36 according to the reference radiation waveform.

In still other embodiments, phantom 35 is positioned in step S401 using the light field and a radiation image is acquired. To determine congruence between the light and radiation fields, distances between one or more holes 36 and one or more edges of the radiation field are determined from the radiation image or from a waveform of the radiation image. In this regard, any edge of the radiation field landing outside of phantom 35 will appear prominently in the image and waveform as described above.

Once the field congruence is determined in step S404 it is determined in step S405 whether the congruence is acceptable. AAPM Task Group suggests that the congruence should be within 2 mm or 1% of the field width, but other standards may be used. If the congruence is not acceptable, the radiation field and/or the light field are adjusted in step S406. The adjustment may proceed automatically based on the lack of congruence determined in step S404. For example, if it is determined that the light field is located 3 mm to the right of the radiation field, light bulb 29 may be adjusted so that the light field moves 3 mm to the left.

If it is determined that the congruence is acceptable in step S405, it is determined whether required gantry positions have been considered in step S407. In this regard, it is useful to determine field congruence at various gantry angles to ensure that the light field does not move relative to the radiation field due to an unstable bulb or mirror when at particular gantry angles. If all required gantry angles have been considered, process steps 400 terminate.

If all required gantry angles have not been considered, the gantry angle is changed in step S408 by rotating gantry 12 around axis 14 to the desired angle. Flow then returns to step S401. Since phantom 35 is positioned normal to beam 15 according to the presently-described embodiment, rotation of gantry 12 may require use of a clamp, bracket or other type of positioning device to hold phantom 35 normal to beam 15.

Those in the art will appreciate that various adaptations and modifications of the above-described embodiments can be configured without departing from the scope and spirit of the invention. For example, embodiments of the present invention may differ from the description of process steps 400. In addition, the particular arrangement of process steps 400 is not meant to imply a fixed order to the steps; embodiments of the present invention can be practiced in any order that is practicable.

Therefore, it is to be understood that, within the scope of the appended claims, the invention may be practiced other than as specifically described herein.

What is claimed is:

1. A method for determining congruence of a light field and a radiation field, comprising:
   acquiring first electronic image data representing a light field produced by a light emitter;
   acquiring second electronic image data representing a radiation field produced by a treatment radiation emitter; and
   determining a congruence between the light field and the radiation field based on the first data and the second data.

2. A method according to claim 1, further comprising:
   controlling the light emitter to emit light; and
   controlling the treatment radiation emitter to emit treatment radiation,
   wherein the emitted light illuminates a phantom located at a first position, the first position between the light emitter and an image data acquisition device, and
   wherein the emitted treatment radiation irradiates the phantom located at the first position, the first position being between the treatment radiation emitter and the image data acquisition device.

3. A method according to claim 1, further comprising:
   prior to acquiring the first electronic image data, setting the light emitter to emit light so as to produce a light field having a particular field size; and
   prior to acquiring the second electronic image data, setting the treatment radiation emitter to emit treatment radiation so as to produce a treatment radiation field having the particular field size.

4. A method according to claim 1, wherein the first electronic image data is acquired by an image acquisition device located at a first position, and
   wherein the second electronic image data is acquired by the image acquisition device located at the first position.

5. A method according to claim 1, further comprising:
   normalizing the first electronic image data and the second electronic image data to account for differences in divergence properties of the emitted light and the emitted treatment radiation,
   wherein the normalized first electronic image data represents a location of a hole of a phantom illuminated by the emitted light,
   wherein the normalized second electronic image data represents a location of an edge of the phantom, and
   wherein the determining step further comprises comparing a distance between the location of the hole and the location of the edge as represented in the superimposed image data with an actual corresponding distance between the hole and the edge of the phantom.

6. A method according to claim 1, further comprising:
   normalizing the first electronic image data and the second electronic image data to account for differences in divergence properties of the emitted light and the emitted treatment radiation,
   wherein the normalized first electronic image data comprises first waveforms representing a phantom as illuminated by the emitted light,
   wherein the normalized second electronic image data comprises second waveforms representing the phantom as irradiated by the treatment radiation, and
   wherein the determining step comprises:
   determining a first location of a hole of the phantom based on the first waveforms;
   determining a second location of the hole of the phantom based on the second waveforms; and
   determining the congruence between the light field and the radiation field based on a difference, if any, between the first location and the second location.

7. A method according to claim 1, further comprising:
   acquiring first reference electronic image data representing a reference light field produced by the light emitter; and
   acquiring second reference electronic image data representing a reference radiation field produced by the treatment radiation emitter,
   wherein the determining step comprises:
   determining a first location of a hole of the phantom based on the first reference electronic image data;
   determining a second location of the hole of the phantom based on the second reference electronic image data;
   determining a third location of the hole of the phantom based on the first electronic image data;
   determining a fourth location of the hole of the phantom based on the second electronic image data; and
   comparing a distance between the first location and the second location with a distance between the third location and the fourth location.

8. A method according to claim 1, wherein the first electronic image data comprises first waveforms representing a phantom as illuminated by the emitted light, and the second electronic image data comprises second waveforms representing the phantom as irradiated by the treatment radiation, further comprising:
   acquiring first reference electronic image data representing a reference light field produced by the light emitter, the first reference electronic image data comprising third waveforms representing a phantom as illuminated in the reference light field; and
   acquiring second reference electronic image data representing a reference radiation field produced by the treatment radiation emitter, the second reference electronic image data comprising fourth waveforms representing the phantom as irradiated in the reference radiation field;

wherein the determining step comprises:
comparing a location of a hole of the phantom according to the first waveforms with a location of the hole according to the third waveforms; and
comparing a location of the hole of the phantom according to the second waveforms with a location of the hole according to the fourth waveforms.

9. A computer-readable medium storing processor-executable process steps to determine congruence of a light field and a radiation field, the process steps comprising:
a step to acquire first electronic image data representing a light field produced by a light emitter;
a step to acquire second electronic image data representing a radiation field produced by a treatment radiation emitter; and
a step to determine a congruence between the light field and the radiation field based on the first data and the second data.

10. A medium according to claim 9, the process steps further comprising:
a step to control the light emitter to emit light; and
a step to control the treatment radiation emitter to emit treatment radiation,
wherein the emitted light illuminates a phantom located at a first position, the first position between the light emitter and an image data acquisition device, and
wherein the emitted treatment radiation irradiates the phantom located at the first position, the first position being between the treatment radiation emitter and the image data acquisition device.

11. A medium according to claim 9, the process steps further comprising:
a step to normalize the first electronic image data and the second electronic image data to account for differences in divergence properties of the emitted light and the emitted treatment radiation,
wherein the normalized first electronic image data represents a location of a hole of a phantom illuminated by the emitted light,
wherein the normalized second electronic image data represents a location of an edge of the phantom, and
wherein the determining step further comprises a step to compare a distance between the location of the hole and the location of the edge with an actual corresponding distance between the hole and the edge of the phantom.

12. A medium according to claim 9, the process steps further comprising:
a step to normalize the first electronic image data and the second electronic image data to account for differences in divergence properties of the emitted light and the emitted treatment radiation,
wherein the normalized first electronic image data comprises first waveforms representing a phantom as illuminated by the emitted light,
wherein the normalized second electronic image data comprises second waveforms representing the phantom as irradiated by the treatment radiation, and
wherein the determining step comprises:
a step to determine a first location of a hole of the phantom based on the first waveforms;
a step to determine a second location of the hole of the phantom based on the second waveforms; and
a step to determine the congruence between the light field and the radiation field based on a difference, if any, between the first location and the second location.

13. A medium according to claim 9, the process steps further comprising:
a step to acquire first reference electronic image data representing a reference light field produced by the light emitter; and
a step to acquire second reference electronic image data representing a reference radiation field produced by the treatment radiation emitter,
wherein the determining step comprises:
a step to determine a first location of a hole of the phantom based on the first reference electronic image data;
a step to determine a second location of the hole of the phantom based on the second reference electronic image data;
a step to determine a third location of the hole of the phantom based on the first electronic image data;
a step to determine a fourth location of the hole of the phantom based on the second electronic image data; and
a step to compare a distance between the first location and the second location with a distance between the third location and the fourth location.

14. A medium according to claim 9, wherein the first electronic image data comprises first waveforms representing a phantom as illuminated by the emitted light, and the second electronic image data comprises second waveforms representing the phantom as irradiated by the treatment radiation, the process steps further comprising:
a step to acquire first reference electronic image data representing a reference light field produced by the light emitter, the first reference electronic image data comprising third waveforms representing a phantom as illuminated in the reference light field; and
a step to acquire second reference electronic image data representing a reference radiation field produced by the treatment radiation emitter, the second reference electronic image data comprising fourth waveforms representing the phantom as irradiated in the reference radiation field,
wherein the determining step comprises:
a step to compare a location of a hole of the phantom according to the first waveforms with a location of the hole according to the third waveforms; and
a step to compare a location of the hole of the phantom according to the second waveforms with a location of the hole according to the fourth waveforms.

15. An apparatus to determine congruence of a light field and a radiation field, comprising:
a memory storing processor-executable process steps;
a processor in communication with the memory and operative in conjunction with the stored process steps to:
acquire first electronic image data representing a light field produced by a light emitter;
acquire second electronic image data representing a radiation field produced by a treatment radiation emitter; and
determine a congruence between the light field and the radiation field based on the first data and the second data.

16. An apparatus according to claim 15, the processor further operative in conjunction with the stored process steps to:
normalize the first electronic image data and the second electronic image data to account for differences in divergence properties of the emitted light and the emitted treatment radiation, wherein the normalized first electronic image data represents a location of a hole of a phantom illuminated by the emitted light, wherein the normalized second electronic image data represents a location of an edge of the phantom, and wherein the determining step further comprises comparison of a distance between the location of the hole and the location of the edge with an actual corresponding distance between the hole and the edge of the phantom.

17. An apparatus according to claim 15, the processor further operative in conjunction with the stored process steps to:

normalize the first electronic image data and the second electronic image data to account for differences in divergence properties of the emitted light and the emitted treatment radiation, wherein the normalized first electronic image data comprises first waveforms representing a phantom as illuminated by the emitted light, wherein the normalized second electronic image data comprises second waveforms representing the phantom as irradiated by the treatment radiation, and wherein the determining step comprises:

determination of a first location of a hole of the phantom based on the first waveforms;

determination of a second location of the hole of the phantom based on the second waveforms; and determination of the congruence between the light field and the radiation field based on a difference, if any, between the first location and the second location.

18. An apparatus according to claim 15, the processor further operative in conjunction with the stored process steps to:

acquire first reference electronic image data representing a reference light field produced by the light emitter; and acquire second reference electronic image data representing a reference radiation field produced by the treatment radiation emitter, wherein the determining step comprises:

determination of a first location of a hole of the phantom based on the first reference electronic image data;

determination of a second location of the hole of the phantom based on the second reference electronic image data;

determination of a third location of the hole of the phantom based on the first electronic image data;

determination of a fourth location of the hole of the phantom based on the second electronic image data; and comparison of a distance between the first location and the second location with a distance between the third location and the fourth location.

19. An apparatus according to claim 15, wherein the first electronic image data comprises first waveforms representing a phantom as illuminated by the emitted light, and the second electronic image data comprises second waveforms representing the phantom as irradiated by the treatment radiation, the processor further operative in conjunction with the stored process steps to:

acquire first reference electronic image data representing a reference light field produced by the light emitter, the first reference electronic image data comprising third waveforms representing a phantom as illuminated in the reference light field; and acquire second reference electronic image data representing a reference radiation field produced by the treatment radiation emitter, the second reference electronic image data comprising fourth waveforms representing the phantom as irradiated in the reference radiation field, wherein the determining step comprises:

comparison of a location of a hole of the phantom according to the first waveforms with a location of the hole according to the third waveforms; and comparison of a location of the hole of the phantom according to the second waveforms with a location of the hole according to the fourth waveforms.

20. A method for determining congruence of a light field and a radiation field, comprising:

acquiring first electronic image data representing a phantom located at a first position and illuminated by light emitted by a light emitter;

acquiring second electronic image data representing the phantom located at the first position and irradiated by treatment radiation emitted by a treatment radiation emitter;

normalizing the first electronic image data and the second electronic image data to account for differences in divergence properties of the emitted light and the emitted treatment radiation;

generating superimposed electronic image data based on the first normalized electronic image data and the second normalized electronic image data;

determining a distance between a location of a hole of the phantom as represented by the first normalized electronic image data and a location of the edge of the phantom as represented by the second normalized electronic image data based on the superimposed electronic image data; and determining a congruence of a light field produced by the light emitter and a treatment radiation field produced by the treatment radiation emitter based on a difference between the distance and an actual corresponding distance between the hole and the edge of the phantom.

21. A computer-readable medium storing processor-executable process steps to determine congruence of a light field and a radiation field, the process steps comprising:

a step to acquire first electronic image data representing a phantom located at a first position and illuminated by light emitted by a light emitter;

a step to acquire second electronic image data representing the phantom located at the first position and irradiated by treatment radiation emitted by a treatment radiation emitter;

a step to normalize the first electronic image data and the second electronic image data to account for differences in divergence properties of the emitted light and the emitted treatment radiation;

a step to generate superimposed electronic image data based on the first normalized electronic image data and the second normalized electronic image data;

a step to determine a distance between a location of a hole of the phantom as represented by the first normalized electronic image data and a location of the edge of the phantom as represented by the second normalized electronic image data based on the superimposed electronic image data; and a step to determine a congruence of a light field produced by the light emitter and a treatment radiation field produced by the treatment radiation emitter based on a difference between the distance and an actual corresponding distance between the hole and the edge of the phantom.

22. A system for determining congruence of a light field and a radiation field, comprising:

a light emitter for emitting light;

a treatment radiation emitter for emitting treatment radiation;

a data acquisition device for acquiring image data based on the emitted light and image data based on the emitted treatment radiation;

a phantom disposed at a location between the light emitter and the data acquisition device and between the treatment radiation emitter and the data acquisition device; and an image processing device, wherein the data acquisition device acquires first electronic image data representing the phantom as illuminated by light emitted by the light emitter and acquires second electronic image data representing the phantom as irradiated by treatment radiation emitted by the treatment radiation emitter, and wherein the image processing device normalizes the first electronic image data and the second electronic image data to account for differences in divergence properties of the emitted light and the emitted treatment radiation, generates superimposed electronic image data based on the first normalized electronic image data and the second normalized electronic image data, determines a distance between a location of a hole of the phantom as represented by the first normalized electronic image data and a location of the edge of the phantom as represented by the second normalized electronic image data based on the superimposed electronic image data, and determines a congruence of a light field produced by the light emitter and a treatment radiation field produced by the treatment radiation emitter based on a difference between the distance and an actual corresponding distance between the hole and the edge of the phantom.

23. A method for determining congruence of a light field and a radiation field, comprising:

acquiring first waveforms representing a phantom located at a first position as illuminated by light emitted by a light emitter;

acquiring second waveforms representing the phantom located at the first position as irradiated by treatment radiation emitted by a treatment radiation emitter;

normalizing the first waveforms and the second waveforms to account for differences in divergence properties of the emitted light and the emitted treatment radiation;

determining a first location of a hole of the phantom based on the first normalized waveforms;

determining a second location of the hole of the phantom based on the second normalized waveforms; and determining the congruence between the light field and the radiation field based on a difference, if any, between the first location and the second location.

24. A computer-readable medium storing processor-executable process steps to determine congruence of a light field and a radiation field, the process steps comprising:

a step to acquire first waveforms representing a phantom located at a first position as illuminated by light emitted by a light emitter;

a step to acquire second waveforms representing the phantom located at the first position as irradiated by treatment radiation emitted by a treatment radiation emitter;

a step to normalize the first waveforms and the second waveforms to account for differences in divergence properties of the emitted light and the emitted treatment radiation;

a step to determine a first location of a hole of the phantom based on the first normalized waveforms;

a step to determine a second location of the hole of the phantom based on the second normalized waveforms; and a step to determine the congruence between the light field and the radiation field based on a difference, if any, between the first location and the second location.

25. A system for determining congruence of a light field and a radiation field, comprising:

a light emitter for emitting light;

a treatment radiation emitter for emitting treatment radiation;

a data acquisition device for acquiring image data based on the emitted light and image data based on the emitted treatment radiation;

a phantom disposed at a location between the light emitter and the data acquisition device and between the treatment radiation emitter and the data acquisition device; and an image processing device, wherein the data acquisition device acquires first waveforms representing the phantom as illuminated by light emitted by the light emitter and acquires second waveforms representing the phantom as irradiated by treatment radiation emitted by the treatment radiation emitter, and wherein the image processing device normalizes the first waveforms and the second waveforms to account for differences in divergence properties of the emitted light and the emitted treatment radiation, determines a first location of a hole of the phantom based on the first normalized waveforms, determines a second location of the hole of the phantom based on the second normalized waveforms, and determines the congruence between the light field and the radiation field based on a difference, if any, between the first location and the second location.

* * * * *